(12) United States Patent
Griffith

(10) Patent No.: US 6,671,349 B1
(45) Date of Patent: Dec. 30, 2003

(54) TOMOSYNTHESIS SYSTEM AND REGISTRATION METHOD

(75) Inventor: Lionell K. Griffith, Solvang, CA (US)

(73) Assignee: Olganix Corporation, Davidson, NC (US)

( * ) Notice: Subject to any disclaimer, the term of this patent is extended or adjusted under 35 U.S.C. 154(b) by 83 days.

(21) Appl. No.: 09/709,586

(22) Filed: Nov. 13, 2000

(51) Int. Cl.⁷ .................................................. G01B 3/00
(52) U.S. Cl. ...................... 378/163; 378/162; 378/205; 378/207; 356/139.1
(58) Field of Search ................................. 378/163, 162, 378/205, 207; 382/131, 151, 289, 294; 250/206.1, 231.11; 356/139.1, 141.1, 141.3, 141.5, 614, 621

(56) References Cited

U.S. PATENT DOCUMENTS

| | | |
|---|---|---|
| 3,499,146 A | 3/1970 | Richards |
| 3,809,886 A | 5/1974 | Cochran et al. |
| 3,830,128 A | 8/1974 | Cochran et al. |
| 3,940,619 A | 2/1976 | Ellingson et al. |
| 4,061,924 A * | 12/1977 | Jacoby et al. ................ 378/162 |
| 4,128,781 A | 12/1978 | Flisikowski et al. |
| 4,188,640 A | 2/1980 | Dittrich et al. |
| 4,207,595 A | 6/1980 | Dittrich et al. |
| 4,246,483 A | 1/1981 | Weiss et al. |
| 4,383,733 A | 5/1983 | Weiss et al. |
| 4,394,063 A | 7/1983 | Weiss et al. |
| 4,469,440 A | 9/1984 | Dallas |
| 4,481,650 A | 11/1984 | Kinanen |
| 4,513,433 A | 4/1985 | Weiss et al. |
| 4,516,252 A | 5/1985 | Linde et al. |
| 4,516,261 A | 5/1985 | Harding et al. |
| 4,566,112 A | 1/1986 | Linde et al. |
| 4,598,369 A | 7/1986 | Wang et al. |
| 4,662,379 A | 5/1987 | Macovski |
| 4,688,241 A | 8/1987 | Peugeot |
| 4,736,396 A | 4/1988 | Boyd et al. |
| 4,769,756 A | 9/1988 | Webber, Richard L. et al. |
| 4,777,360 A * | 10/1988 | Carner, Jr. ................ 250/206.1 |
| 4,836,206 A | 6/1989 | Maxwell et al. |
| 4,888,794 A | 12/1989 | Haaker et al. |
| 4,903,204 A | 2/1990 | Dobbins, III |
| 5,014,293 A | 5/1991 | Boyd et al. |
| 5,020,086 A | 5/1991 | Peugeot |
| 5,040,539 A | 8/1991 | Schmitt et al. |
| 5,212,720 A * | 5/1993 | Landi et al. ................ 378/206 |
| 5,214,686 A | 5/1993 | Webber |
| 5,237,998 A | 8/1993 | Duret et al. |
| 5,359,637 A | 10/1994 | Webber |
| 5,511,106 A | 4/1996 | Doebert et al. |
| 5,544,157 A | 8/1996 | Wenstrup et al. |
| 5,561,696 A | 10/1996 | Adams et al. |
| 5,576,551 A * | 11/1996 | Adair ....................... 250/472.1 |
| 5,583,904 A | 12/1996 | Adams |
| 5,592,562 A | 1/1997 | Rooks |
| 5,598,454 A | 1/1997 | Franetzki et al. |
| 5,621,811 A | 4/1997 | Roder et al. |
| 5,666,392 A | 9/1997 | Ploetz |
| 5,668,844 A | 9/1997 | Webber |
| 5,671,297 A | 9/1997 | Koppe et al. |

(List continued on next page.)

FOREIGN PATENT DOCUMENTS

WO 99/44503 9/1999

*Primary Examiner*—Drew A. Dunn
(74) *Attorney, Agent, or Firm*—Fulbright & Jaworski (57) ABSTRACT

An apparatus for representing an internal structure of an object includes an energy source, an energy sensor for sensing energy from the energy source and generating image data pertaining to an object disposed proximate the energy sensor and exposed to energy from the energy source, and a processor programmed to manipulate image data obtained from the energy source as a function of an actual orientation between the radiation source and the energy sensor from which an image of the object can be generated. A method is also disclosed.

52 Claims, 6 Drawing Sheets

U.S. PATENT DOCUMENTS

| | | |
|---|---|---|
| 5,687,209 A | 11/1997 | Adams |
| 5,717,734 A | 2/1998 | Lee-Kin et al. |
| 5,719,952 A | 2/1998 | Rooks |
| 5,782,762 A | 7/1998 | Vining |
| 5,794,620 A | 8/1998 | Dossel et al. |
| 5,828,722 A | 10/1998 | Ploetz et al. |
| 5,872,828 A | 2/1999 | Niklason et al. |
| 5,878,104 A | 3/1999 | Ploetz |
| 5,885,215 A | 3/1999 | Dossel et al. |
| 5,896,437 A | 4/1999 | Ploetz |
| 5,920,319 A | 7/1999 | Vining et al. |
| 5,967,979 A | 10/1999 | Taylor et al. |
| 5,999,836 A | 12/1999 | Nelson et al. |
| 6,002,739 A | 12/1999 | Heumann |
| 6,005,907 A | 12/1999 | Ploetz |
| 6,028,910 A | 2/2000 | Kirchner et al. |
| 6,081,577 A | 6/2000 | Webber |
| 6,083,162 A | 7/2000 | Vining |

* cited by examiner

TOMOSYNTHESIS SYSTEM AND REGISTRATION METHOD

FIELD OF THE INVENTION

The present invention involves a method and apparatus of registering or calibrating a tomosynthesis system. In particular, the present invention is directed to a rapid and accurate method of registering an energy source to a sensor surface in a tomosynthesis system.

BACKGROUND AND SUMMARY

In a number situations is useful to view the detailed internal structures of solid objects or to see inside of objects that are opaque to the visible spectrum. In medical applications, for example, it is desirable to non-invasively detect structural details of bone or tissue within a human body or other living organism. The diagnosis and treatment of disease and injury often depends upon such capabilities. Other applications include, for example, the nondestructive testing and inspection of material joints, electronic assemblies, and other intricate devices or high value articles. Similarly, it is also useful to inspect and examine objects and containers for the presence of contraband, listening devices, explosives or dangerous materials.

Several conventional techniques have been used to view internal structures with varying degrees of success. Most of these conventional systems use energy in the form of penetrating radiation, such as x-rays or gamma rays. Magnetic resonance imaging (MRI) systems can also be used to view internal information. The conventional systems, however, tend to be time consuming, expensive and have severe limitations in terms of the amount of visual information provided about detailed internal structures of objects such as soft tissues and the surface characteristics of internal organs of human bodies.

Most conventional systems involve the use of penetrating radiation directed through the object onto radiographic film or a bank of electronic radiation detectors. One such conventional technique, computed tomography (CT), involves a radiation source mounted in view of a row of radiation detectors. An object placed between the radiation source and the detectors is rotated to expose a section of the object to radiation from several angles. The data collected by the radiation detectors is processed to generate a two-dimensional slice of the internal structure of the object. To obtain a three-dimensional view, a number of slices of the object must be taken at discrete distances and, even then, information will often be lacking between slices. Hence, conventional CT techniques are not particularly well suited for the generation of three-dimensional views since the object must be exposed to additional radiation for each slice.

U.S. Pat. No. 4,167,672 to Richards pertains to another conventional technique known as dynamic tomography or tomosynthesis. In accordance with this technique, the object is exposed to radiation from a number of angles, with each exposure recorded on a separate piece of radiographic film. The set of radiographs may be viewed by superimposing and appropriately aligning them to bring an image plane into focus. This tomosynthesis technique avoids the overexposure problem of the single slice CT systems, since the object is subjected to a fewer number exposures to obtain three-dimensional information for the object. Obtaining three-dimensional information with tomosynthesis can be quite difficult, however, due to problems such as film and equipment misalignment and inaccuracies. Also, the task of adjusting or manipulating a stack of radiographs to obtain a clear three-dimensional image or a desired image can be enormously complex. Also, images can only be viewed in planes which are parallel to one of the film planes in the set of radiographs.

Figure 1:
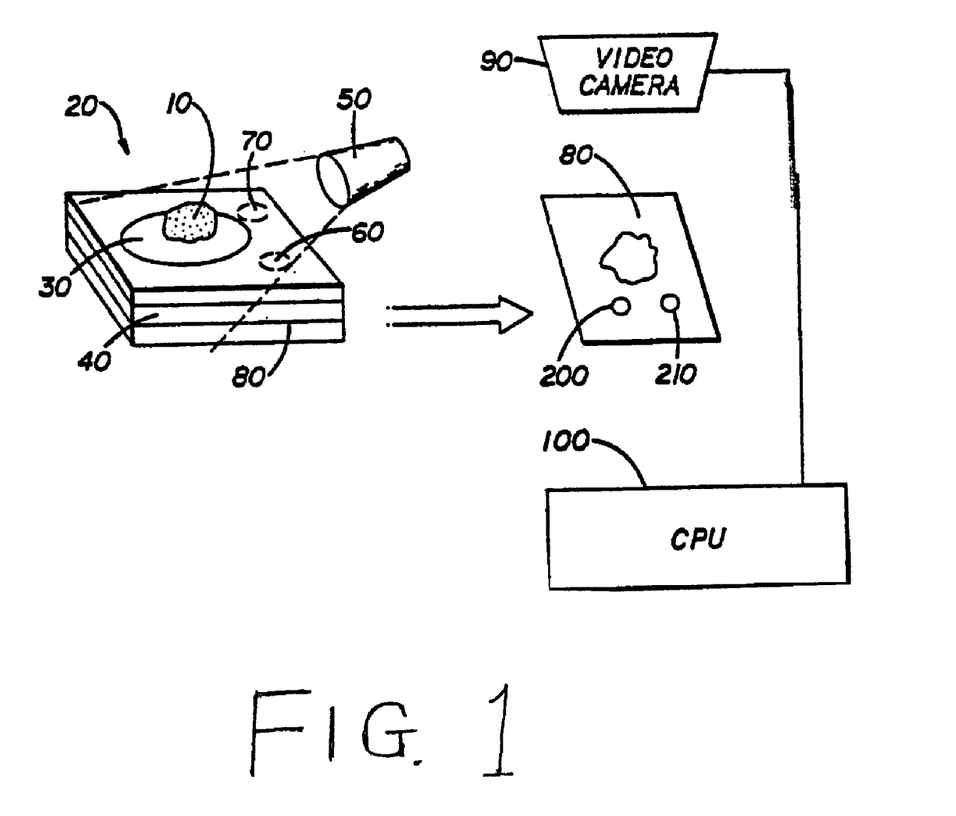
FIG. 1 is a schematic, perspective view of a portion of an embodiment of a tomosynthesis system such as is disclosed in U.S. Pat. No. 5,070,454 to the present inventor.

FIG. 1 depicts a portion of the tomosynthesis system 100 disclosed in U.S. Pat. No. 5,070,454 to the present inventor. In the system of FIG. 1, an object 10 is placed on platform assembly 20 for examination. The platform assembly comprises rotation plate 30 made of a material that is substantially transparent to penetrating radiation, and a film cassette 40 for holding radiographic film sheets 80. The rotation plate 30 may be rotated so as to expose the object 10 to radiation at a number of different rotational positions relative to radiation source 50. The '454 patent explains the invention in terms of having eight different rotational positions, but discloses that different numbers of rotational positions can be used in accordance with the invention. Two circular reference markers 60 and 70 made of a high-density radiation opaque substance are mounted in the platform assembly 20 between the rotation plate 30 and the film cassette 40. In accordance with one embodiment of the '454 patent, the reference markers 60 and 70 are positioned to form an equilateral triangle between their centers at the base of the triangle and the center of the rotation plate 30 at the apex of the triangle.

To collect images of the object 10 for tomosynthesis, a new radiographic film sheet 80 is used at each rotation position to capture an exposure from the radiation source 50. That is, each sheet of radiographic film 80 records a radiographic image of the object 10 at one of the eight distinct angular orientations. A video camera 90 can be used to digitize the images of the developed radiographic film sheets 80 containing the radiation shadows of the object 10 and the reference markers 60 and 70. The digitized images may then be supplied to a computer 101 for further processing.

In accordance with the novel tomosynthesis system disclosed in the '454 patent, the shadow images of the object 10 must be properly aligned to bring the tomosynthesis image into focus and view the planes at various depths of the object 10. The dual reference markers 60 and 70 are used to properly aligned the shadow images and thus register the shadow images of the radiographic film sheets 80 which have radiation shadows of the object 10 from various angles. This allows an operator of the tomosynthesis apparatus to select a level or series of levels desired for viewing selected internal structural images of the object 10.

Embodiments of the '454 patent have the two registration marks of the reference markers 60 and 70 on each of the exposed radiographic film sheets 80 containing shadow images from a different position. The two registration marks facilitate appropriate registration of align the exposed radiographic film sheets 80 for tomosynthesis and can be used to address matters such as errors due to equipment orientation and misorientation. One drawback to the use of the two registration marks on the rotatable platform is that the marks occupy space on the platform, as well as on the developed radiographic film, that could otherwise be used to support an object to be studied. Because of the expense of film and the increased difficulty in accurately registering equipment as the size of the equipment gets larger, it would be desirable to limit the amount of space in a tomosynthesis system that must be dedicated to determining rotational position and ensuring appropriate equipment registration.

Also, in accordance with the present invention, the inventor realized that the two planar reference markers 60 and 70 do not always provide sufficient information about the orientation of the radiation source 50 relative to the platform assembly 20. By having the two registration marks on each radiographic film sheet 80, such relative orientation information was not necessary. Such information is useful in embodiments of the present invention using a plate sensor instead of radiographic film sheets. Particularly for tomosynthesis using a plate sensor or sensor assembly instead of radiographic film sheets, it is advantageous to know the precise alignment and relative orientation of the energy source and the sensor.

The present invention permits rapidly and accurately registering a sensor source to a sensor surface in a tomosynthesis system.

In accordance with one aspect of the present invention, a method of determining an orientation of an energy source relative to an energy sensor having a sensor surface is disclosed. According to the method, a first registration marker is placed on a marker location proximate the sensor surface. A first shadow image corresponding to the first registration marker is obtained with the sensor surface by exposing the first registration marker to energy from the energy source. A second registration marker is placed at a predetermined height above the marker location on the surface. A second shadow image corresponding to the second registration marker is obtained with the sensor surface by exposing the second registration marker to energy from the energy source. A location of the first shadow image and a location of the second shadow image are compared to determine an orientation between the energy source and the sensor surface.

In accordance with another aspect of the present invention, a method of obtaining an object image in a tomosynthesis system, the system including an energy source and an energy sensor having a sensor surface, is disclosed. According to the method, an orientation of the energy source relative to the sensor is determined. An object is positioned proximate the sensor surface. One or more object shadow images are obtained with the energy sensor by exposing the object to energy from the energy source. The one or more object shadow images are manipulated as a function of the orientation between the energy source and the sensor surface.

In accordance with yet another aspect of the present invention, a tomosynthesis system including a registration arrangement includes an energy source, and a sensor adapted detect energy from the energy source and having a sensor surface. The system further includes a first registration marker adapted to be removably disposed at a marker location proximate the sensor surface, and a second registration marker adapted to be removably disposed at a predetermined height above the marker location. A processor is provided for comparing locations of shadow images of the first registration marker and the second registration marker obtained by the sensor by exposing the first registration marker and the second registration marker to energy from the energy source to determine an orientation of the energy source relative to the sensor surface.

In accordance with still another aspect of the present invention, an apparatus for representing an internal structure of an object includes an energy source, an energy sensor for sensing energy from the energy source and generating image data pertaining to an object disposed proximate the energy sensor and exposed to energy from the energy source, and a processor programmed to manipulate image data obtained from the energy source as a function of an actual orientation between the radiation source and the energy sensor from which an image of the object can be generated.

BRIEF DESCRIPTION OF THE DRAWINGS

The features and advantages of the present invention are well understood by reading the following detailed description in conjunction with the drawings in which like numerals indicate similar elements and in which.

DETAILED DESCRIPTION OF THE PREFERRED EMBODIMENTS

Figure 2:
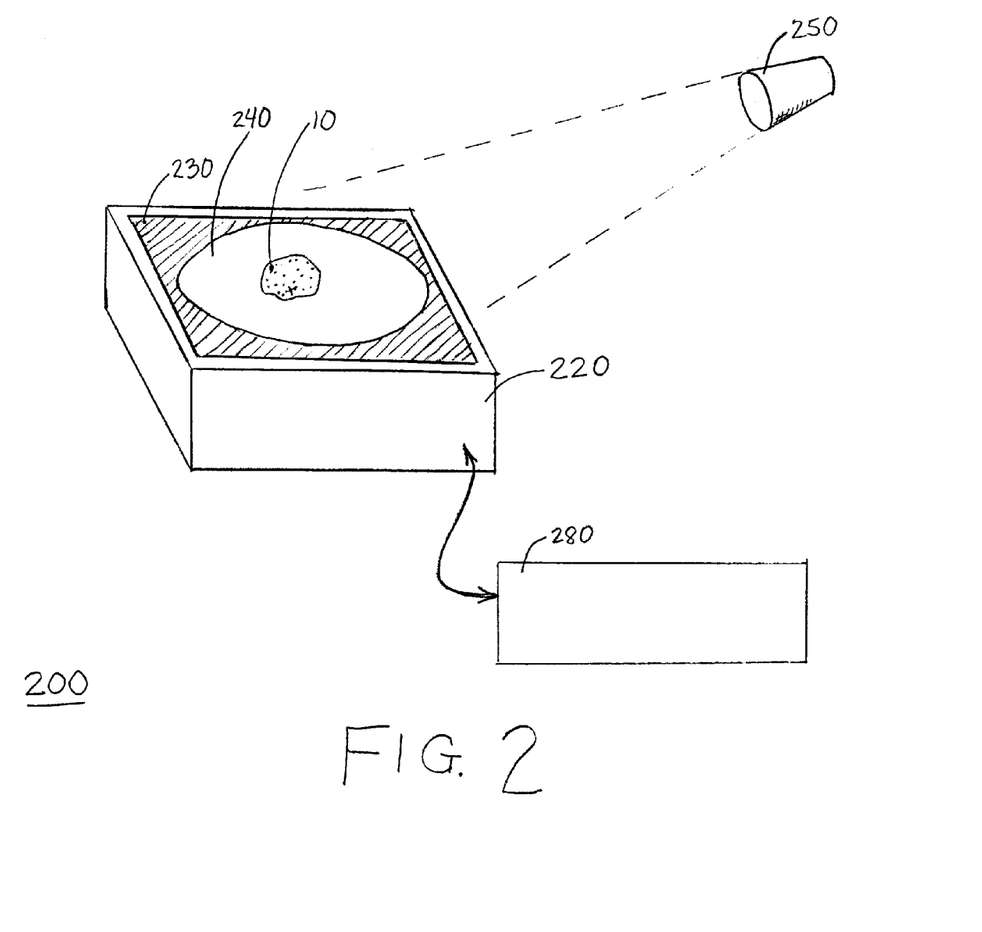
FIG. 2 is a schematic, perspective view of a tomosynthesis system according to an embodiment of the present invention.

FIG. 2 shows a tomosynthesis system 200 which may be used in accordance with the present invention. The tomosynthesis system 200 has a sensor assembly 220, an energy source such as a radiation source 250, and a data processor or computer 280. The processor or computer 280 will be understood to include conventional image viewing means such as a computer screen (not shown).

The sensor assembly 220 includes a sensor surface 230, on top of which is positioned a rotation plate 240 made of a substance essentially transparent to energy from the energy source 250. For purposes of the present discussion, reference will generally be made to an energy source in the form of a radiation source 250, and a sensor plate 230 adapted to detect radiation, however, it will be appreciated that the present invention is also applicable to systems using energy sources and sensors that involve other forms of energy.

The rotation plate 240 is adapted to be oriented to different positions so as to expose an object 10 to radiation at a number of different rotational positions relative to the radiation source 250. It will, however, be appreciated that other arrangements are also possible and appropriate, such as where the plate 240 is stationary and the radiation source 250 circles the plate so that the object 10 is exposed to radiation at different rotational positions, where multiple radiation sources 250 are arranged at different positions around the sensor surface 230, and where both the radiation source 250 and the object 10 are moved to permit exposure of the object to radiation from different perspectives. For convenience of discussion, however, the embodiment wherein the rotation plate 240 turns the object 10 relative to a stationary radiation source 250 will be discussed, except where otherwise noted.

The radiation source 250 may generate radiation in any suitable form, such as x-rays, gamma rays, or any other like type of radiation that, preferably, is capable of penetrating the object 10. Other embodiments of the invention may involve the use of energy in other suitable forms that are capable of being detected by some form of sensor, such as sound or magnetic waves. The sensor surface 230 is preferably a digital flat panel radiation detector or other suitable radiation sensor which can detect radiation from the radiation source. The sensor surface 230 may be made of an array of pixels, detectors, or any other suitable form of sensors capable of detecting incident energy, such as radiation, from the radiation source 250. The sensor surface 230 may comprise either a single sensor plate or device, or multiple sensor plates or sensor devices interconnected together to be larger than one sensor for use with a large sized object 10. If desired or necessary, the sensor surface may be a film-based sensor as was used in the prior art systems of U.S. Pat. No. 5,051,904, U.S. Pat. No. 5,070,454 or U.S. Pat. No. 5,319,550, which are incorporated by reference.

For the purposes of illustration, it will be assumed that it has been attempted to align the radiation source 250 substantially along a central axis of the sensor surface 230. However, the radiation source 250 may be aligned in any other suitable orientation relative to the sensor surface 230 such as, for example, diagonally across the sensor surface 230 from corner to corner. The present invention facilitates determination of precisely what the relative positions of the various elements of the tomosynthesis system actually are, regardless of any attempts to initially register the elements relative to one another.

In a preferred embodiment, the rotation plate 240 is substantially flat and level relative to the sensor surface 230, and preferably made of a substance essentially transparent to the penetrating radiation of the radiation source 250. The rotation plate 240, upon which the object 10 is placed, is rotatable about a central point by known manual, mechanical, or electro-mechanical means to a number of different rotational positions. The movement and positioning of the rotation plate 240 may be effected by a stepper motor or other servo mechanism under the control of the computer 280 or under the control of a dedicated controller. Alternatively, the rotation plate 240 may be may be manually turned relative to the radiation source 250 and the sensor 230. It is preferred to know precisely the angle through which the rotation plate 240 has been turned relative to a starting point to facilitate data processing. Views from as many different angular positions as desired may be taken, with both the level of detail of the object views that can be obtained and the difficulty in processing the visual data obtained ordinarily increasing as more views are taken.

To collect images of the object 10 using the tomosynthesis system 200, the radiation source 250 is controlled to expose the object 10 to radiation at various rotational positions. The rotation plate 240 and the object 10 to be examined are oriented on the sensor surface 230 so that radiation passing through the object 10 casts a shadow image of the object 10 onto the sensor surface 230 for each of the rotational positions of interest. The sensor surface 230 detects the shadow image, and communicates signals corresponding to the detected radiation to the computer 280 for storage in memory.

The stored shadow image data is preferably subjected to data processing as part of the tomosynthesis process. The data processing involves manipulating and matching the locations of various points (ordinarily pixels when using a digital flat panel radiation detector) on the various shadow images obtained by exposing the object and the sensor to radiation at the different rotational positions to create a tomosynthesis image. The computations performed by the computer 280 can be based on a presumed orientation of the radiation source relative to the sensor surface 230. In processing the image data to use in creating a tomosynthesis image, it is necessary to know the actual orientation of the radiation source 250 relative to the sensor surface 230 to permit appropriate manipulation of data to correct for differences between the actual orientation of those elements and the presumed orientation of the elements upon which the image generation calculations are based. However, the use of two opaque reference markers, as described in the Background section and shown as reference markers 60 and 70 of FIG. 1, does not always or conveniently provide sufficient information about the relative orientation of the radiation source 250 and the sensor surface 230.

It will be appreciated that there are numerous suitable techniques by which the computer 280 can be programmed to process image data to generate an image of an object, such as a three-dimensional image. These techniques are already known or are believed to be capable of being generated by one skilled in data processing and the present invention is not considered to require any particular technique of data processing. However, an aspect of the invention pertains to manipulation, preferably by means of the computer and suitable data processing software, of image information based on information relating to the relative positions or orientation of an energy source and an energy sensor.

Figure 3A:
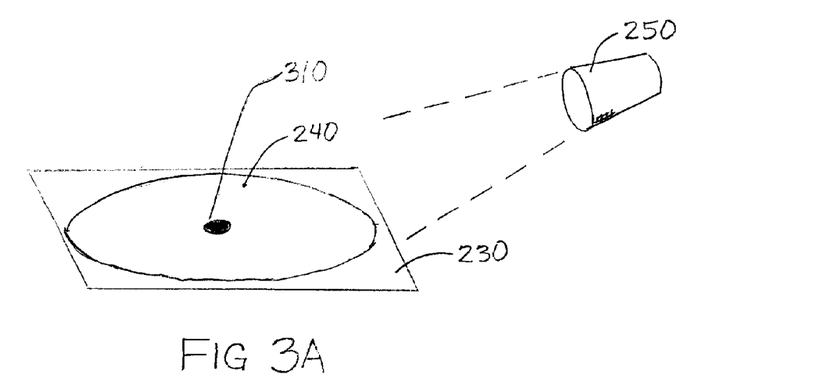
FIGS. 3A–3B are schematic, perspective views of a tomosynthesis system including registration equipment according to embodiments of the present invention.
Figure 3B:
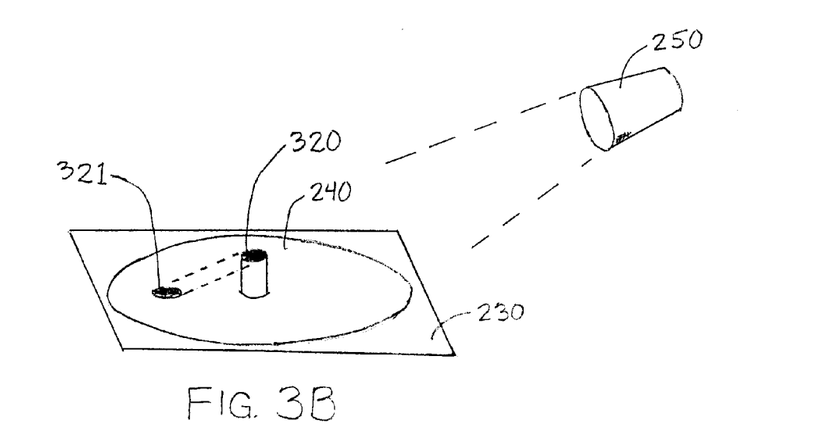

FIGS. 3A–3B show apparatus for registration of a tomosynthesis system, in accordance with the present invention, which provides information about the relative orientation of the radiation source 250 and the sensor surface 230. FIG. 3A shows an opaque first registration marker 310 to be positioned proximate the sensor assembly 220 for registration purposes. By "proximate" it is meant that the first registration marker 310 is to be positioned directly on the sensor surface 230 itself or on a structure disposed above the sensor surface 230 for holding the object 10 such as the rotation plate 240. The first registration marker 310 is preferably ordinarily disposed above the sensor surface 230 on the rotation plate 240. In accordance with preferred embodiments of the present invention, the first registration marker 310 is positioned substantially in the center of the rotation plate 240. For example, in accordance with one embodiment, at least some portion of the first registration marker 310 covers the center of rotation of the rotation plate 240. If desired or necessary, the first registration marker 310 may be located in positions on the rotation plate 240 other than the center of rotation of the rotation plate.

Figure 3C:
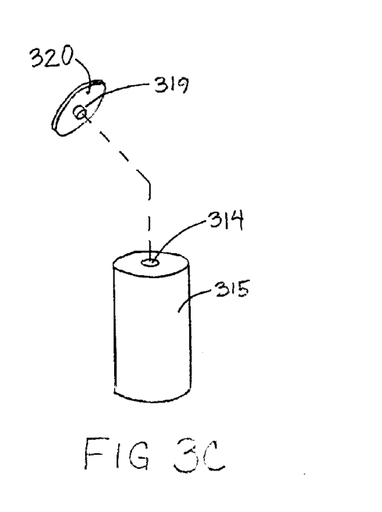
FIGS. 3C–3D are schematic, perspective views of portions of a registration system according to embodiments of the present invention.

The rotation plate 240 is preferably marked, scribed or recessed in a manner which is transparent to radiation yet indicates the center of rotation of the rotation plate 240 for placement of the first registration marker 310, or provided with other like means of centering the marker. For example, in one embodiment the first registration marker 310 has a protuberance extending from one side that fits into a hole or recess of the rotation plate 240. The protuberance of the first registration marker 310 may be in the form of the protuberance 319 shown on the registration marker 320 of FIG. 3C. The protuberance of the first registration marker 310 is positioned within a recessed portion or hole in the rotation plate 240 so as to center the first registration marker 310 at the center of rotation of the rotation plate 240.

One method of checking to verify that the first registration marker 310 is centered is by controlling the radiation source 250 to expose the sensor assembly 220 to radiation at two or more different rotational positions of the rotation plate 240. A shadow image of the first registration marker 310 disposed on the rotation plate 240 is projected onto the sensor plate 230 at each of the two or more different positions. For a uniformly circular first registration marker 310 disposed on a rotation plate 240 that is flat and level relative to the sensor surface 230, the shadow images obtained from projection of the first registration marker 310 onto the sensor plate 230 at any two rotational positions should completely coincide. If the shadow images do not coincide, either the first registration marker 310 is not centered at the center of rotation of the rotation plate 240, or the orientation between at least one pair of the sensor surface 230, the rotation plate 240, and the radiation source 250, was inadvertently varied between exposures. Where the relative locations of the sensor surface 230, the rotation plate 240, and the radiation source 250 are tightly controlled, non-coinciding shadow images can generally be presumed to be due to an off-center first registration marker 310. The computer 280 can be programmed to appropriately manipulate image data, if necessary, when the shadow images do not coincide. An alternative technique of determining whether the first registration marker 310 is centered can simply involve taking appropriate physical measurements to locate the center of rotation of the rotation plate 240.

FIG. 3B depicts a tomosynthesis system registration apparatus with a registration post 315 and a second registration marker 320 in accordance with the present invention. The second registration marker 320 is preferably identical to the first registration marker 310 and may, if desired or necessary, be the same marker. The second registration marker 320 and the post 315 are configured such that the second registration marker sits on top the registration post shown in FIG. 3C. In a preferred embodiment, the registration post 315 is made of a material which is substantially transparent to radiation from the radiation source 250, while the second registration marker 320 is substantially opaque to radiation from the radiation source 250.

The registration post 315 is configured to stand upright, preferably at a 90° angle to the surface of the rotation plate 240. The upright orientation of the registration post 315 with the second registration marker 320 sitting atop may be determined in a manner similar to that described above for the first registration marker 310 wherein the shadow images of the second registration marker 320 taken at two different angular positions are compared to see if they coincide. That is, the radiation source 250 may be controlled to expose the sensor assembly 220 to radiation at two or more different angular positions by rotating the rotation plate 240 between exposures. The second registration marker 320 sitting atop the registration post 315 casts image shadows at each position of radiation exposure which are detected by the sensor surface 230. If the second registration marker 320 is uniformly circular and the registration post 315 is properly oriented at an upright 90°, and there are no other orientation errors due to the sensor surface 230, the rotation plate 240, or the radiation source 250, the shadow images cast upon the sensor surface 230 at any two rotational positions of the rotation plate 240 should completely coincide.

The height of the registration post 315 is selected such that the shadow images of the second registration marker 320 from the radiation source 250 fall upon the sensor surface 230, i.e., not beyond the limitations of the sensor surface 230. Therefore, the height of the registration post 315 depends upon the angle of inclination of the radiation source 250 relative to the sensor surface 230. For example, since the radiation source 250 casts a longer shadow when it forms a smaller angle with the sensor surface 230 than when it forms a larger angle, the height of the registration post 315 must be selected so that the shadow image of the second registration marker 320 falls upon a desired portion of the sensor surface 230.

Figure 3D:
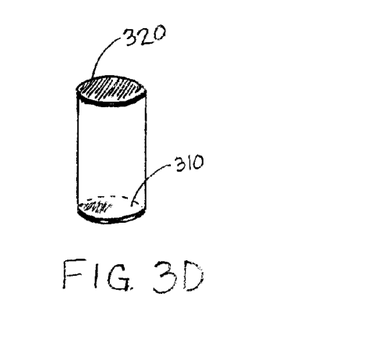

FIG. 3D depicts an alternative embodiment of the present invention in which the first registration marker 310 is attached to one end of the registration post 315 and the second registration marker 320 is attached to the other end of the registration post 315. In accordance with this embodiment, the registration post 315 is preferably of sufficient length such that the shadow images of the two registration markers 310 and 320 do not overlap for a given inclination at which the radiation source 250 is to be used. By having the two registration markers 310 and 320 respectively attached to either end of the registration post 315, only one exposure to the radiation source 250 is needed to obtain a shadow image for both the first registration marker 310 and the second registration marker 320.

Figure 4A:
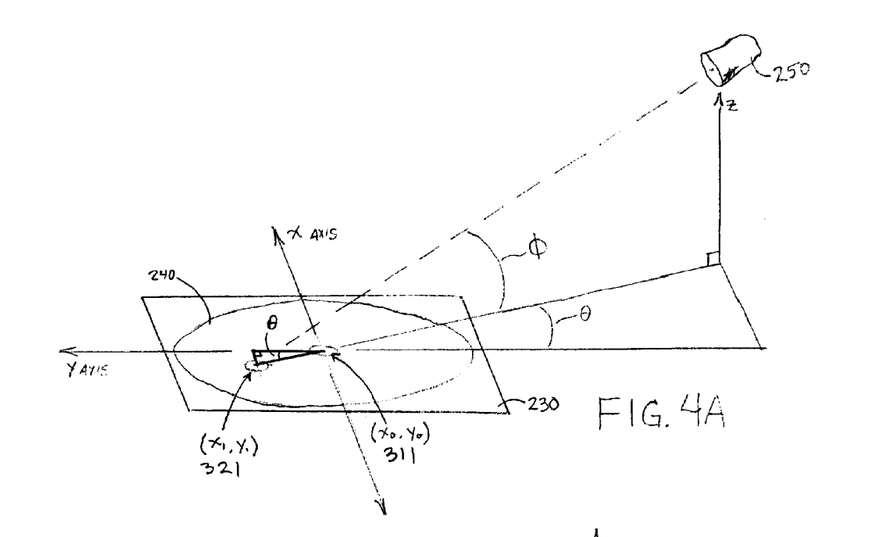
FIGS. 4A–4C are perspective, top, and side views, respectively, of a tomosynthesis system having shadow images of registration markers formed according to the present invention.
Figure 4B:
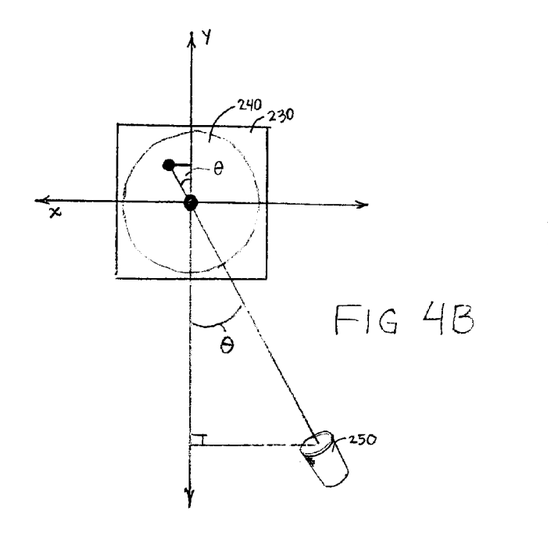
Figure 4C:
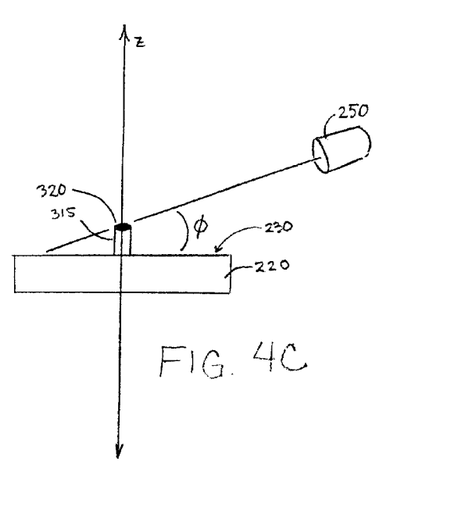

FIG. 4A is a perspective view depicting shadow image positions 311 ($x_0$, $y_0$) and 321 ($x_1$, $y_1$) on the sensor surface 230 corresponding to the first registration marker 310 and the second registration marker 320, respectively. FIG. 4B is the top view of the same tomosynthesis system arrangement, and FIG. 4C is the side view. The shadow image position information corresponding to the two registration markers 310 and 320 is used to determine the orientation of the radiation source 250 relative to the sensor surface 230. The two shadow images 311 and 321 are centered at coordinates ($x_0$, $y_0$) and ($x_1$, $y_1$) of a coordinate system, respectively, where the "y" axis will be understood to be an arbitrarily located straight line along the sensor surface 230, preferably on a long axis of the surface, and with which it has been attempted to the radiation source 250 so that energy emitted from the radiation source travels along the y-axis. An x-axis is perpendicular to the y-axis and lies in the same horizontal plane. Locations of the centers ($x_0$, $y_0$) and ($x_1$, $y_1$) of the shadow images 311 and 321, respectively, can be mathematically determined. Alternatively, if desired or necessary, the present invention may use measurements taken from an edge or other predetermined point on the shadow images. Points other than the center of the shadow images may be preferred when, for example, non-circular registration markers are used.

The angle of misalignment of the radiation source 250 from the central axis is depicted as angle θ in FIGS. 4A and 4B. The angle of inclination of the radiation source 250 from the plane of the sensor surface 230 is depicted as φ in FIGS. 4A and 4C. Both the angle of misalignment θ and the angle of inclination φ may be determined through geometric calculations based upon the position information for the shadow image 311 and the shadow image 321, such as the following relationships:

$$\theta = \arcsin\{(x_1-x_0)/[(x_1-x_0)^2+(y_1-y_0)^2]^{1/2}\} \quad (1)$$

$$\phi = \arcsin\{[h/[h^2+(y_1-y_0)^2]^{1/2}\} \quad (2)$$

In the above relationship, h is the height of the top of the second registration marker 320 above the sensor surface, which is preferably the known height of the registration post 315 plus the height of the second registration marker 320 plus the distance from the top of the rotation plate 240 to the sensor surface 230. Other suitable coordinate systems for specifying positions and angles may be used to describe the positions and angular orientation of the shadow images 311 and 321.

Figure 5:
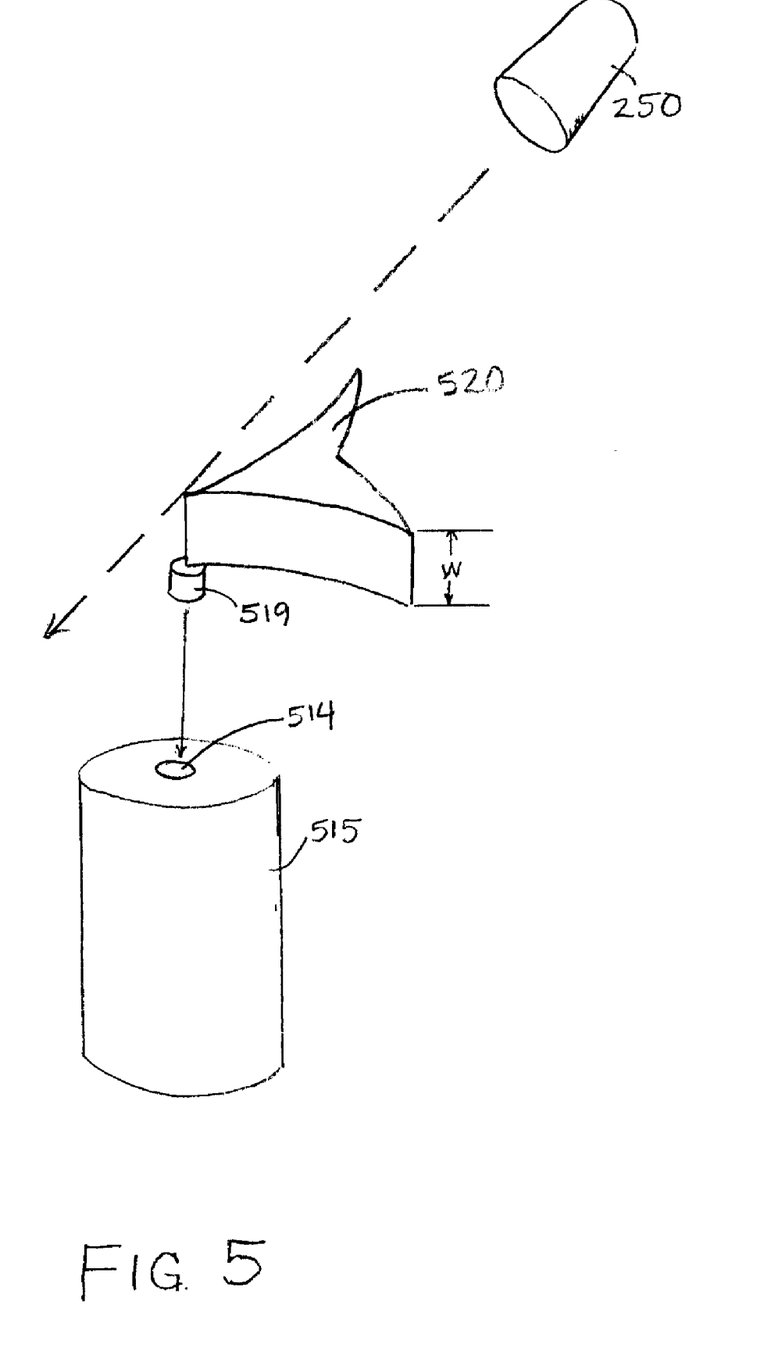
FIG. 5 is a schematic, perspective view of an embodiment of a registration marker according to an embodiment of the present invention.

FIG. 5 is an alternative embodiment of a registration marker in accordance with the present invention. The present invention has been disclosed above in terms of a circular registration marker, e.g., the registration marker 320 of FIG. 3C. In accordance with alternative embodiments, shapes other than circular may be used for registration markers in accordance with the present invention. For example, a shape such as that illustrated in FIG. 5 may be used. The registration marker 520 corresponds to the registration marker 320 and is used in the same way with the exception of where the "center" of the registration marker 520 is defined to be. For the registration marker 520, the point of the arrow indicates the "center" position discussed above for the purposes of determining the angle of misalignment θ and the angle of inclination φ using equations (1) and (2), or like geometry functions.

Preferred embodiments of registration markers such as the registration marker 520 are preferably designed so that the means of fastening and centering the markers on their corresponding posts do not interfere with the path of radiation from the radiation source 250. That is, the protuberances 519 fall within the shadow cast by the registration marker 520. In one embodiment, the width w of the registration marker 520 is such that the extending portion of the protuberance 519 does not interfere with the path of radiation. Alternatively, a structural means of fastening the protuberance to the marker may be provided so as to avoid radiation interference.

Figure 6:
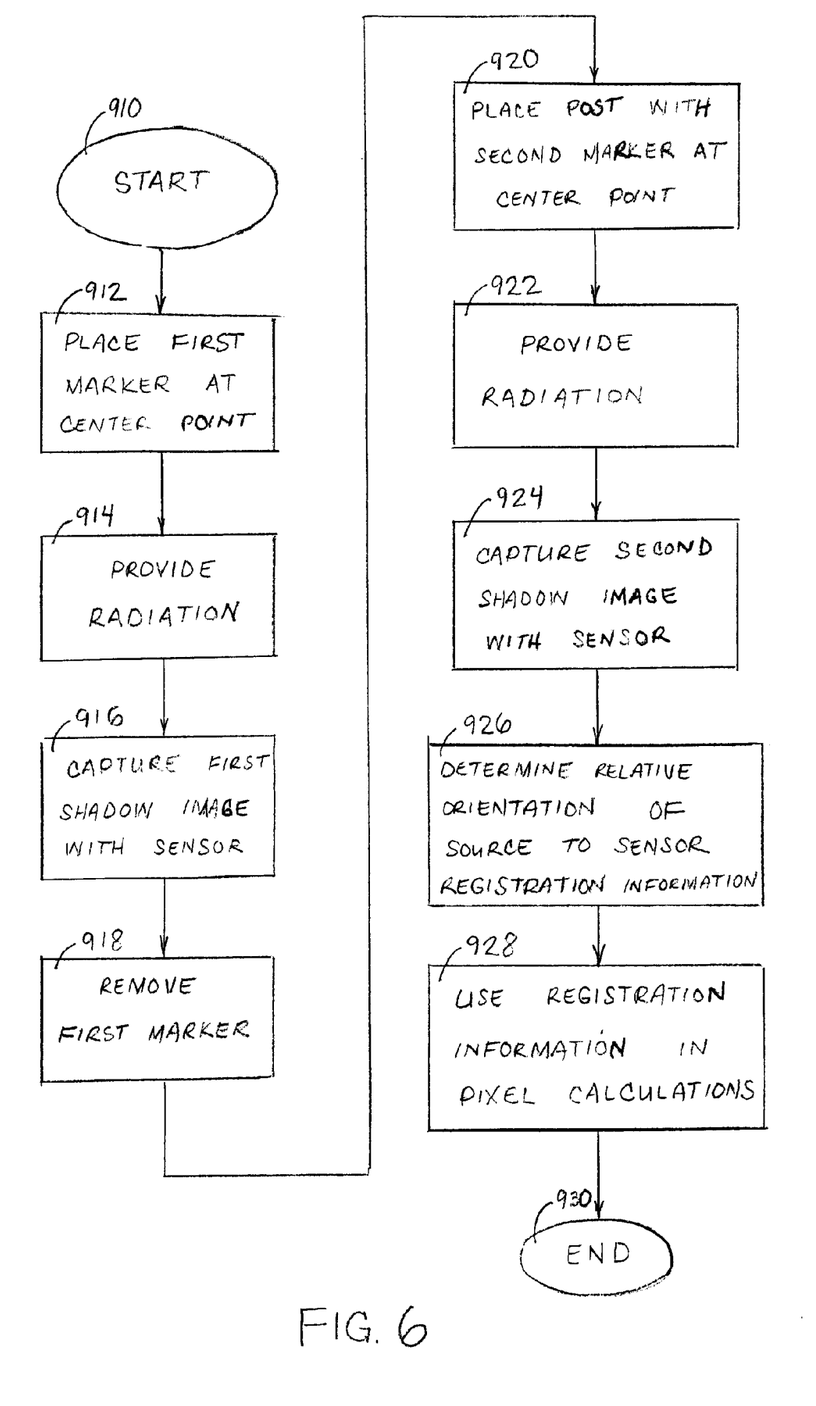
FIG. 6 is a flowchart representing steps in a method of registering a tomosynthesis system according to an embodiment of the present invention.

FIG. 6 shows steps in a method of registering a tomosynthesis system in accordance with the present invention. The method is described with reference to the apparatus shown in FIG. 2, but may alternatively be used with other apparatus embodiments of the present invention or like tomosynthesis systems.

The method begins at step 910, and proceeds to step 912 in which first registration marker 310 is placed on the rotation plate 240, preferably at a center point of the plate. At step 914 the radiation source 250 emits radiation and the sensor assembly 220 and the first registration marker 310 on the rotation plate 240 are exposed to the radiation so that a shadow corresponding to the first registration marker 310 is projected onto the sensor surface 230 of the sensor assembly 220. The sensor surface 230 then provides information to the computer 280 which generates the shadow image 311 in accordance with step 916.

Following step 916, the first registration marker 310 is removed from the rotation plate 240 in step 918. The registration post 315 with the second registration marker 320 is positioned on the rotation plate 240 in step 920, again, preferably at the center of rotation of the plate, with the post preferably perpendicular to the sensor plate 230. In step 922 the radiation source 250 emits radiation and the sensor assembly 220 and the second registration marker 320 on the rotation plate 240 are exposed to the radiation so that a shadow corresponding to the second registration marker 320 is projected onto the sensor surface 230 of the sensor assembly 220. The sensor surface 230 then provides information to the computer 280 which generates the shadow image 321 in accordance with step 924.

Once step 924 has been completed, the information for registration of the tomosynthesis system will have been collected. The method proceeds from step 924 to step 926 in which calculations are performed based upon the geometric relationship of the detected shadow images 311 and 321 and the height h of the second registration marker 320 in order to determine the nature of the orientation of the sensor surface 230 to the radiation source 250. After step 926, the registration markers 310 and 320 are removed. An object is positioned on the rotation plate and exposed to radiation at the various rotational positions so that image data pertaining to each position is detected by the sensor plate 230 and transmitted to the computer 280. The registration information obtained at step 926 is used in computations (herein "pixel calculations") by the computer 280 at step 928 to manipulate data pertaining to the various object images to correct for equipment misalignments and facilitate generation of accurate images of the object at any desired angle and from any desired position.

Advantages of the tomosynthesis system 200 and method wherein orientation of elements of the system is determined using the first and second reference markers 310 and 320 include the ease with which orientation can be determined. Moreover, orientation can be determined prior to obtaining object images so the reference markers need not be present in images of the object. Further still, once the orientation of the elements of a tomosynthesis system is determined according to the present invention, it may not ever be necessary to determine the orientation again, although periodic checks of the orientation will likely be desirable to ensure that elements have not been inadvertently moved relative to one another.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A method of determining an orientation of an energy source relative to an energy sensor having a sensor surface, comprising the steps of:

placing a first registration marker that is substantially opaque to energy levels of interest on a marker location proximate the sensor surface;

obtaining a first shadow image corresponding to the first registration marker by exposing the first registration marker to energy from the energy source;

placing a second registration marker that is substantially opaque to energy levels of interest at a predetermined height above the marker location on the surface;

the space between the first and second markers including a region that is translucent to energy levels of interest;

obtaining a second shadow image corresponding to the second registration marker by exposing the second registration marker to energy from the energy source; and comparing a location of the first shadow image and a location of the second shadow image to determine an orientation between the energy source and the sensor surface.

2. The method as set forth in claim 1, wherein the first and second registration markers are substantially opaque to energy levels of interest.

3. The method as set forth in claim 1, wherein the marker location is disposed on a plate that is rotatable relative to the sensor surface, the method comprising the further step of locating a center of rotation of the plate.

4. The method as set forth in claim 3, wherein the center of rotation of the plate is determined by rotating the plate through a predetermined angle, obtaining a third shadow image of one of the first registration marker and the second registration marker, and comparing a location of the third shadow image to a location of one of the first shadow image and the second shadow image.

5. The method as set forth in claim 4, wherein the center of rotation is disposed at a center of the marker location.

6. The method as set forth in claim 1, wherein the first registration marker and the second registration marker are the same size.

7. The method as set forth in claim 1, wherein the first registration marker and the second registration marker are the same marker.

8. The method as set forth in claim 7, wherein the second registration marker is supported at the predetermined height by a pedestal.

9. The method as set forth in claim 8, wherein the pedestal is substantially transparent to energy at levels of interest.

10. The method as set forth in claim 1, wherein the orientation between the energy source and the sensor surface comprises information including at least one of an angle of misalignment and an angle of inclination.

11. The method as set forth in claim 10, wherein the orientation between the energy source and the sensor surface comprises both the angle of misalignment and the angle of inclination.

12. The method as set forth in claim 1, wherein the energy source is a radiation source.

13. The method as set forth in claim 1, wherein the energy sensor is a flat panel digital detector.

14. A method of obtaining an object image in a tomosynthesis system, the system including an energy source and an energy sensor having a sensor surface, comprising the steps of:

placing a first registration marker that is substantially opaque to energy levels of interest on a marker location proximate the sensor surface, obtaining a first shadow image corresponding to the first registration marker by exposing the first registration marker to energy from the energy source, placing a second registration marker that is substantially opaque to energy levels of interest at a predetermined height above the marker location on the surface, the space between the first and second markers including a region that is translucent to energy levels of interest;

obtaining a second shadow image corresponding to the second registration marker by exposing the second registration marker to energy from the energy source, and comparing locations of the first shadow image and the second shadow image to determine the orientation between the energy source and the sensor surface;

positioning an object proximate the sensor surface;

obtaining one or more object shadow images with the energy sensor by exposing the object to energy from the energy source; and manipulating the one or more object shadow images as a function of the orientation between the energy source and the sensor surface.

15. The method as set forth in claim 14, further comprising the steps of: rotating at least one of the energy source and the object about a center of rotation to a plurality of rotational positions; obtaining an object shadow image at each of the plurality of rotational positions by exposing the object to energy from the energy source at each of the plurality of rotational positions; combining object shadow images obtained at the plurality of rotational positions to obtain a three-dimensional image of the object; and manipulating the three-dimensional image of the object as a function of the orientation between the energy source and the sensor surface.

16. The method as set forth in claim 15, wherein the object is positioned on a plate disposed above the energy sensor.

17. The method as set forth in claim 16, wherein the plate is rotatable relative to the energy sensor.

18. The method as set forth in claim 14, wherein the orientation between the energy source and the sensor surface comprises information including at least one of an angle of misalignment and an angle of inclination.

19. The method as set forth in claim 18, wherein the orientation between the energy source and the sensor surface comprises both the angle of misalignment and the angle of inclination.

20. The method as set forth in claim 14, wherein the energy source is a radiation source.

21. The method as set forth in claim 14, wherein the energy sensor is a flat panel digital detector.

22. A tomosynthesis system including a registration arrangement, comprising:

an energy source;

a sensor adapted detect energy from the energy source and having a sensor surface;

a first registration marker that is substantially opaque to energy levels of interest and is adapted to be removably disposed at a marker location proximate the sensor surface;

a second registration marker that is substantially opaque to energy levels of interest and is adapted to be removably disposed at a predetermined height above the marker location;

the space between the first and second markers including a region that is translucent to energy levels of interest; and a processor for comparing locations of shadow images of the first registration marker and the second registration marker obtained by the sensor by exposing the first registration marker and the second registration marker to energy from the energy source to determine an orientation of the energy source relative to the sensor surface.

23. The system as set forth in claim 22, further comprising a plate disposed above the sensor surface, the marker location being disposed on the rotation plate.

24. The system as set forth in claim 23, wherein the plate is rotatable relative to the sensor surface.

25. The system as set forth in claim 22, wherein the first registration marker and the second registration marker are connected to each other.

26. The system as set forth in claim 25, wherein the first registration marker and the second registration marker are connected to each other by a pedestal made of a different material than the first registration marker and the second registration marker.

27. The system as set forth in claim 22, wherein the first registration marker and the second registration marker are discrete from each other.

28. The system as set forth in claim 22, wherein the orientation between the energy source and the sensor surface comprises information including at least one of an angle of misalignment and an angle of inclination.

29. The system as set forth in claim 28, wherein the orientation between the energy source and the sensor surface comprises both the angle of misalignment and the angle of inclination.

30. An apparatus for representing an internal structure of an object, comprising:

an energy source;

an energy sensor for sensing energy from the energy source and generating image data pertaining to an object disposed proximate the energy sensor and exposed to energy from the energy source;

a first reference marker that is substantially opaque to energy levels of interest and that is adapted to be removably disposed on a marker location proximate the energy sensor, and a second reference marker that is substantially opaque to energy levels of interest and is adapted to be removably disposed at a predetermined height above the marker location, and wherein the processor compares image data pertaining to relative locations of images of the first reference marker and the second reference marker to determine the orientation between the energy source and the energy sensor, and a processor programmed to manipulate image data obtained from the energy source as a function of an actual orientation between the radiation source and the energy sensor from which an image of the object can be generated.

31. The apparatus as set forth in claim 30, further comprising a plate disposed proximate the energy sensor for supporting the object relative to the energy sensor.

32. The apparatus as set forth in claim 31, wherein the plate is rotatable relative to the energy sensor.

33. The apparatus as set forth in claim 30, wherein at least one of the energy source and the object are movable to a plurality of different locations.

34. The apparatus as set forth in claim 33, wherein the processor is programmed to combine object image data obtained by the energy sensor by exposing the object to energy from the energy source at the plurality of different locations and to generate a three-dimensional image of the object therefrom.

35. The apparatus as set forth in claim 30, wherein the orientation between the energy source and the energy sensor comprises information including at least one of an angle of misalignment and an angle of inclination.

36. The apparatus as set forth in claim 35, wherein the orientation between the energy source and the energy sensor comprises both the angle of misalignment and the angle of inclination.

37. A method of determining an orientation of an energy source relative to an energy sensor having a sensor surface, comprising the steps of:

placing a first registration marker on a marker location proximate the sensor surface, the marker location being disposed on a plate that is rotatable relative to the sensor surface;

obtaining a first shadow image corresponding to the first registration marker by exposing the first registration marker to energy from the energy source;

placing a second registration marker at a predetermined height above the marker location on the surface;

obtaining a second shadow image corresponding to the second registration marker by exposing the second registration marker to energy from the energy source;

comparing a location of the first shadow image and a location of the second shadow image to determine an orientation between the energy source and the sensor surface;

locating a center of rotation of the plate.

38. The method as set forth in claim 37, wherein the center of rotation of the plate is determined by rotating the plate through a predetermined angle, obtaining a third shadow image of one of the first registration marker and the second registration marker, and comparing a location of the third shadow image to a location of one of the first shadow image and the second shadow image.

39. The method as set forth in claim 37, wherein the center of rotation is disposed at a center of the marker location.

40. A method of determining an orientation of an energy source relative to an energy sensor having a sensor surface, comprising the steps of:

placing a first registration marker on a marker location proximate the sensor surface;

obtaining a first shadow image corresponding to the first registration marker by exposing the first registration marker to energy from the energy source;

placing a second registration marker at a predetermined height above the marker location on the surface;

obtaining a second shadow image corresponding to the second registration marker by exposing the second registration marker to energy from the energy source; and comparing a location of the first shadow image and a location of the second shadow image to determine an orientation between the energy source and the sensor surface that comprises information including at least one of an angle of misalignment and an angle of inclination.

41. The method as set forth in claim 40 wherein the orientation between the energy source and the sensor surface comprises both the angle of misalignment and the angle of inclination.

42. A method of obtaining an object image in a tomosynthesis system, the system including an energy source and an energy sensor having a sensor surface, comprising the steps of:

determining an orientation of the energy source relative to the sensor;

positioning an object proximate the sensor surface;

rotating at least one of the energy source and the object about a center of rotation to a plurality of rotational positions;

obtaining an object shadow image at each of the plurality of rotational positions by exposing the object to energy from the energy source at each of the plurality of rotational positions;

combining object shadow images obtained at the plurality of rotational positions to obtain a three-dimensional image of the object; and manipulating the three-dimensional image of the object as a function of the orientation between the energy source and the sensor surface.

43. The method as set forth in claim 42, wherein the object is positioned on a plate disposed above the energy sensor.

44. The method as set forth in claim 43, wherein the plate is rotatable relative to the energy sensor.

45. A method of obtaining an object image in a tomosynthesis system, the system including an energy source and an energy sensor having a sensor surface, comprising the steps of:

determining an orientation of the energy source relative to the sensor;

positioning an object proximate the sensor surface;

obtaining one or more object shadow images with the energy sensor by exposing the object to energy from the energy source; and manipulating the one or more object shadow images as a function of the orientation between the energy source and the sensor surface that comprises information including at least one of an angle of misalignment and an angle of inclination.

46. The method as set forth in claim 45, wherein the orientation between the energy source and the sensor surface comprises both the angle of misalignment and the angle of inclination.

47. A tomosynthesis system including a registration arrangement, comprising:

an energy source;

a sensor adapted to detect energy from the energy source and having a sensor surface;

a plate disposed above the sensor surface rotatable relative to the sensor surface;

a first registration marker adapted to be removably disposed at a marker location proximate the sensor surface;

a second registration marker adapted to be removably disposed at a predetermined height above the marker location; and a processor for comparing locations of shadow images of the first registration marker and the second registration marker obtained by the sensor by exposing the first registration marker and the second registration marker to energy from the energy source to determine an orientation of the energy source relative to the sensor surface.

48. A tomosynthesis system including a registration arrangement, comprising:

an energy source;

a sensor adapted to detect energy from the energy source and having a sensor surface;

a first registration marker adapted to be removably disposed at a marker location proximate the sensor surface;

a second registration marker adapted to be removably disposed at a predetermined height above the marker location; and a processor for comparing locations of shadow images of the first registration marker and the second registration marker obtained by the sensor by exposing the first registration marker and the second registration marker to energy from the energy source to determine an orientation of the energy source relative to the sensor surface that comprises information including at least one of an angle of misalignment and an angle of inclination.

49. The system as set forth in claim 48, wherein the orientation between the energy source and the sensor surface comprises both the angle of misalignment and the angle of inclination.

50. An apparatus for representing an internal structure of an object, comprising:

an energy source;

an energy sensor for sensing energy from the energy source and generating image data pertaining to an object disposed proximate the energy sensor and exposed to energy from the energy source;

a plate disposed proximate the energy sensor for supporting the object relative to the energy sensor the plate being rotatable relative to the energy sensor; and a processor programmed to manipulate image data obtained from the energy source as a function of an actual orientation between the radiation source and the energy sensor from which an image of the object can be generated.

51. An apparatus for representing an internal structure of an object, comprising:

an energy source;

an energy sensor for sensing energy from the energy source and generating image data pertaining to an object disposed proximate the energy sensor and exposed to energy from the energy source; and a processor programmed to manipulate image data obtained from the energy source as a function of an actual orientation between the radiation source and the energy sensor from which an image of the object can be generated, the orientation comprising information including at least one of an angle of misalignment and an angle of inclination.

52. The apparatus as set forth in claim 51, wherein the orientation between the energy source and the energy sensor comprises both the angle of misalignment and the angle of inclination.

* * * * *